(12) United States Patent
Croisetière et al.

(10) Patent No.: US 10,386,279 B2
(45) Date of Patent: Aug. 20, 2019

(54) METHOD AND APPARATUS FOR PREPARING AN ANALYTICAL SAMPLE BY FUSION

(71) Applicant: MATERIAUX NIEKA INC., Quebec (CA)

(72) Inventors: Louis Croisetière, Stoneham (CA); Arnaud Noblesse, Quebec (CA)

(73) Assignee: MATERIAUX NIEKA INC., Quebec (CA)

( * ) Notice: Subject to any disclaimer, the term of this patent is extended or adjusted under 35 U.S.C. 154(b) by 143 days.

(21) Appl. No.: 15/511,045

(22) PCT Filed: Sep. 14, 2015

(86) PCT No.: PCT/CA2015/050886
§ 371 (c)(1),
(2) Date: Mar. 14, 2017

(87) PCT Pub. No.: WO2016/041063
PCT Pub. Date: Mar. 24, 2016

(65) Prior Publication Data
US 2017/0276580 A1    Sep. 28, 2017

Related U.S. Application Data

(60) Provisional application No. 62/050,246, filed on Sep. 15, 2014.

(51) Int. Cl.
*B01L 3/04*    (2006.01)
*G01J 5/00*    (2006.01)
(Continued)

(52) U.S. Cl.
CPC .......... *G01N 1/44* (2013.01); *G01J 5/00* (2013.01); *G01J 5/12* (2013.01); *G01N 1/4044* (2013.01);
(Continued)

(58) Field of Classification Search
CPC . B01L 3/04; C30B 15/14; C30B 15/20; Y10T 117/1088
See application file for complete search history.

(56) References Cited

U.S. PATENT DOCUMENTS 2,675,853 A * 4/1954 Hatch ............... C04B 30/00
106/417
4,175,610 A * 11/1979 Zauhar ............... C30B 29/06
164/122.2
(Continued)

OTHER PUBLICATIONS

Sericite Safety Data Sheet, Kobo, Oct. 16, 2014.*
International Search Report in co-pending, related PCT/CA2015/050886, dated Nov. 24, 2015.

*Primary Examiner* — David A Rogers
(74) *Attorney, Agent, or Firm* — Thomas | Horstemeyer, LLP (57) ABSTRACT

There is provided a method for preparing an analytical sample by fusion. A mixture of a sample and flux material is heated and stirred, in a crucible, at a temperature sufficient to fuse the mixture and obtain a substantially homogeneous fused mixture; a first portion of heat radiation radiating from the crucible is reflected back to the crucible so as to provide additional heat to fuse the mixture, while heating and stirring the mixture; and the homogeneous fused mixture, is subsequently cooled, thereby forming the analytical sample.

23 Claims, 7 Drawing Sheets

(51) Int. Cl.
  *G01J 5/12*    (2006.01)
  *G01N 1/40*    (2006.01)
  *G01N 1/44*    (2006.01)
  *C30B 15/14*   (2006.01)

(52) U.S. Cl.
  CPC .................. *B01L 3/04* (2013.01); *C30B 15/14* (2013.01); *Y10T 117/1088* (2015.01)

(56) References Cited

U.S. PATENT DOCUMENTS

| | | | | |
|---|---|---|---|---|
| 5,248,378 A * | 9/1993 | Oda | ............... | C30B 15/14 117/217 |
| 5,313,047 A | 5/1994 | O'Brien et al. | | |
| 5,315,091 A * | 5/1994 | O'Brien | ............... | F27B 17/02 164/136 |
| 5,942,032 A * | 8/1999 | Kim | ............... | C30B 15/14 117/13 |
| 6,663,709 B2 * | 12/2003 | Lu | ............... | C30B 15/14 117/13 |
| 8,337,616 B2 * | 12/2012 | Abe | ............... | C30B 15/16 117/11 |
| 8,403,025 B2 * | 3/2013 | Boivin | ............... | B22D 21/025 164/47 |
| 8,591,993 B2 * | 11/2013 | Higashi | ............... | C23C 16/4401 117/200 |
| 8,821,610 B2 * | 9/2014 | Baudis | ............... | B22F 9/22 420/417 |
| 8,955,399 B2 * | 2/2015 | Kanipayor | ............... | B01L 3/04 73/863 |
| 9,222,920 B2 * | 12/2015 | Hirano | ............... | G01N 1/4022 |
| 9,651,463 B2 * | 5/2017 | Schramm | ............... | G01N 1/44 |
| 10,145,024 B2 * | 12/2018 | Lee | ............... | C30B 29/06 |
| 2001/0029036 A1 | 10/2001 | Landers et al. | | |
| 2007/0259992 A1 * | 11/2007 | Tamura | ............... | B82Y 30/00 523/210 |
| 2008/0035050 A1 * | 2/2008 | Sakurada | ............... | C30B 15/14 117/13 |
| 2009/0130619 A1 * | 5/2009 | Okada | ............... | F27B 14/0806 432/158 |
| 2009/0176642 A1 * | 7/2009 | Tomura | ............... | C04B 35/484 501/104 |
| 2010/0024718 A1 * | 2/2010 | Orschel | ............... | C30B 15/203 117/15 |
| 2010/0229785 A1 * | 9/2010 | Abe | ............... | C30B 15/16 117/13 |
| 2010/0303125 A1 * | 12/2010 | Bonnard | ............... | G01K 17/00 374/36 |
| 2012/0024232 A1 * | 2/2012 | Lee | ............... | C23C 14/12 118/726 |
| 2012/0186512 A1 * | 7/2012 | Orschel | ............... | C30B 15/203 117/202 |
| 2013/0049247 A1 * | 2/2013 | Boivin | ............... | B22D 21/025 264/85 |
| 2013/0135724 A1 * | 5/2013 | Funaki | ............... | C30B 15/00 359/484.03 |
| 2014/0142216 A1 * | 5/2014 | Lai | ............... | C08K 3/26 523/339 |
| 2014/0261155 A1 * | 9/2014 | Kimbel | ............... | C30B 15/12 117/31 |
| 2015/0160106 A1 * | 6/2015 | Kanipayor | ............... | B01L 3/04 436/160 |
| 2015/0291799 A1 * | 10/2015 | Gruner | ............... | C09C 1/003 502/242 |
| 2016/0010920 A1 * | 1/2016 | Ingham | ............... | F27D 1/0003 378/44 |
| 2016/0011128 A1 * | 1/2016 | Las Navas Garcia | ... | G01N 1/44 374/14 |
| 2016/0161377 A1 * | 6/2016 | Bornefeld | ............... | G01N 1/286 65/17.3 |

\* cited by examiner

METHOD AND APPARATUS FOR PREPARING AN ANALYTICAL SAMPLE BY FUSION

CROSS-REFERENCE TO RELATED APPLICATIONS

This application is the 35 U.S.C. § 371 national stage application of PCT Application No. PCT/CA2015/050886, filed Sep. 14, 2015, which claims priority to and the benefit of U.S. Provisional Application 62/050,246, filed Sep. 15, 2014, the entire disclosures of which are incorporated herein by reference.

FIELD

The technical field generally relates to the field of sample preparation and, more particularly, to the field of analytical sample preparation by fusion.

BACKGROUND

Preparing analytical samples by fusion for X-ray fluorescence (XRF), atomic absorption (AA) or inductively induced plasma (ICP) analysis typically includes mixing a sample with a flux material, such as lithium tetraborate or lithium metaborate, and heating the mixture to a temperature sufficient to melt the flux material and dissolve the sample to form a homogeneous fused mixture. The homogeneous fused mixture is generally subsequently poured either into a preheated mold to obtain a glass disk suitable for XRF analysis, or into a solution-containing container, such as a beaker, to obtain a solution suitable to be analyzed by AA, ICP or another wet chemistry analysis.

The mixture is typically heated in crucibles provided in a heat furnace (such as a fluxer) to temperatures of approximately 1000° C. At such temperatures, energy losses in the form of heat radiation radiating from the crucibles can be significant. It can thus be desirable to reduce the energy required for heating the mixture.

Further, if the temperature of the homogeneous fused mixture exceeds 1100° C. for a certain time period, some volatile elements such as sodium, chlorine and/or fluorine can start to evaporate from the sample, thereby affecting the subsequent analyses. For at least this reason, it can be desirable to measure and/or control the temperature of the mixture. Existing solutions include measuring the temperature of the mixture by directly measuring the temperature of the crucible using either a type R thermocouple or a pyrometer. However, both the type R thermocouple and the pyrometer can lead to an increase in manufacturing costs for the manufacturer, as well as maintenance costs for the user. Furthermore, the use of a pyrometer is often impractical, as the temperature reading from the pyrometer directly depends on the emissivity value of the crucible surface, which typically changes over time with normal laboratory use, thereby affecting the temperature measurements.

The preparation of analytical samples by fusion still poses a number of challenges.

SUMMARY

In some implementations, there is provided a method for preparing an analytical sample by fusion, comprising: heating and stirring, in a crucible, a mixture of a sample and a flux material at a temperature sufficient to fuse the mixture and obtain a substantially homogeneous fused mixture; while heating and stirring the mixture, reflecting a first portion of heat radiation radiating from the crucible back to the crucible so as to provide additional heat to fuse the mixture; and cooling the substantially homogeneous fused mixture, thereby forming the analytical sample.

In some implementations, the step of reflecting the heat radiation is performed using a reflective surface provided around of and at a distance from the crucible.

In some implementations, the distance is between 0.2 cm and 5 cm.

In some implementations, the reflective surface is an inner surface of a hollow tube.

In some implementations, the reflective surface is also heat-conducting, the method further comprising: indirectly measuring the temperature of the crucible, comprising: absorbing a second portion of the heat radiation radiating from the crucible into the heat-conducting and reflective surface; measuring the temperature of the heat-conducting and reflective surface; and calculating the temperature of the crucible from the temperature of the heat-conducting and reflective surface in accordance with a predetermined correlation between the temperature of the crucible and the temperature of the heat-conducting and reflective surface.

In some implementations, the measuring of the temperature of the heat-conducting and reflective surface is performed using a temperature sensor provided on the heat-conducting and reflective surface.

In some implementations, there is provided a method for preparing an analytical sample by fusion, comprising: heating and stirring, in a crucible, a mixture of a sample and a flux material at a temperature sufficient to fuse the mixture and obtain a substantially homogeneous fused mixture; indirectly measuring the temperature of the crucible, comprising: absorbing at least a portion of heat radiation radiating from the crucible into a heat-conducting surface provided at a distance from the crucible; measuring the temperature of the heat-conducting surface; and calculating the temperature of the crucible from the temperature of the heat-conducting surface in accordance with a predetermined correlation between the temperature of the crucible and the temperature of the heat-conducting surface; and cooling the substantially homogeneous fused mixture, thereby forming the analytical sample.

In some implementations, the measuring of the temperature of the heat-conducting surface is performed using a temperature sensor provided on the heat-conducting surface.

In some implementations, the method further comprises adjusting the temperature of the crucible to a target temperature.

In some implementations, the predetermined correlation is stored in a computer readable storage medium.

In some implementations, the calculating is performed by a processor.

In some implementations, the heating of the mixture is performed by direct heating of the crucible.

In some implementations, the method further comprises pouring the substantially homogeneous fused mixture into a container.

In some implementations, the container is a mould or a solution-containing container.

In some implementations, the step of cooling the substantially homogeneous fused mixture comprises letting the substantially homogeneous fused mixture cool to ambient temperature.

In some implementations there is provided a method for preparing an analytical sample by fusion, comprising: heating and stirring, in a crucible, a mixture of a sample and a flux material at a temperature sufficient to fuse the mixture and obtain a substantially homogeneous fused mixture; while heating and stirring the mixture, reflecting a first portion of heat radiation radiating from the crucible back to the crucible using an inner surface of a hollow tube surrounding the crucible and provided at a distance from the crucible, so as to provide additional heat to fuse the mixture; indirectly measuring the temperature of the crucible, comprising: absorbing a second portion of the heat radiation radiating from the crucible into the hollow tube; measuring the temperature of the hollow tube; and calculating the temperature of the crucible from the temperature of the hollow tube in accordance with a predetermined correlation between the temperature of the crucible and the temperature of the hollow tube; and allowing the substantially homogeneous fused mixture to cool, thereby forming the analytical sample.

In some implementations, there is provided an apparatus for preparing an analytical sample by fusion, comprising: a crucible for receiving a mixture of a sample and a flux material; a crucible support for supporting the crucible; a heater configured to heat the crucible and fuse the mixture to obtain a fused mixture; a stirring unit for stirring the fused mixture in the crucible; and a reflective surface provided around of and at a distance from the crucible, to reflect a first portion of heat radiation radiating from the crucible back to the crucible.

In some implementations, the distance is between 0.2 cm and 5 cm.

In some implementations, the reflective surface is an inner surface of a hollow tube surrounding the crucible.

In some implementations, the apparatus further comprises an insulating surface surrounding the hollow tube to insulate the hollow tube.

In some implementations, the insulating surface is made of aluminium.

In some implementations, the hollow tube has an outer insulating surface made of an insulating material to insulate the hollow tube.

In some implementations, the outer insulating surface is made of an insulating ceramic material.

In some implementations, the reflective surface is also heat-conducting and absorbs a second portion of the heat radiation radiating from the crucible, the apparatus further comprising: a temperature sensor for measuring the temperature of the heat-conducting and reflective surface.

In some implementations, the temperature sensor comprises a thermocouple attached to the heat-conducting and reflective surface.

In some implementations, the apparatus further comprises a processor for calculating the temperature of the crucible from the temperature of the heat-conducting and reflective surface in accordance with a predetermined correlation between the temperature of the crucible and the temperature of the heat-conducting surface.

In some implementations, the reflective surface comprises a heat resistant iron-chromium-aluminium alloy.

In some implementations, there is provided an apparatus for preparing an analytical sample by fusion, comprising: a crucible for receiving a mixture of a sample and a flux material; a crucible support for supporting the crucible; a heater configured to heat the crucible and fuse the mixture to obtain a fused mixture; a stirring unit for stirring the fused mixture in the crucible; a heat-conducting surface provided around of and at a distance from the crucible, to absorb at least a portion of heat radiation radiating from the crucible; and a temperature sensor for measuring the temperature of the heat-conducting surface.

In some implementations, the temperature sensor comprises a thermocouple attached to the heat-conducting surface.

In some implementations, the apparatus further comprises a processor operatively connected to the temperature sensor for calculating the temperature of the crucible from the temperature of the heat-conducting surface in accordance with a predetermined correlation between the temperature of the crucible and the temperature of the heat-conducting surface.

In some implementations, the heat-conducting and reflective surface comprises a heat resistant iron-chromium-aluminium alloy.

In some implementations, the apparatus further comprises a temperature controller for adjusting the temperature of the crucible to a target temperature.

In some implementations, there is provided an apparatus for preparing an analytical sample by fusion, comprising: a crucible for receiving a mixture of a sample and a flux material; a crucible support for supporting the crucible; a heater configured to heat the crucible and fuse the mixture to obtain a fused mixture; a stirring unit for stirring the fused mixture in the crucible; a hollow tube provided at a distance from the crucible and surrounding the crucible, the hollow tube having an inner surface reflecting a first portion of heat radiation radiating from the crucible back to the crucible and absorbing a second portion of the heat radiation; and a temperature sensor for measuring the temperature of the hollow tube.

DETAILED DESCRIPTION

Various techniques that are described herein enable preparation of analytical samples by fusion of a sample and a flux material, suitable for example for XRF, AA or ICP analysis.

It is understood that the term "fusion" (or fuse in verb form) refers to the act of transforming a heterogeneous mixture of the sample and flux material into a melted mixture by heating. The transformation of the heterogeneous mixture into the melted mixture can occur by melting the flux material and dissolving the sample into the melted flux material or by melting and blending both components (i.e., the flux material and the sample) to obtain the melted mixture.

It is understood that the term "analytical sample" refers to a sample to be analyzed, which is treated prior to analysis so as to render the sample responsive to the analytical technique to be used.

It is understood that the flux material typically has a melting temperature lower than the melting temperature of the sample and can, upon melting, act as a solvent to solubilize the sample. For example, the flux material can include a salt such as lithium tetraborate, lithium metaborate or a mixture thereof.

In one general aspect, there is provided an apparatus for preparing an analytical sample by fusion.

Figure 1:
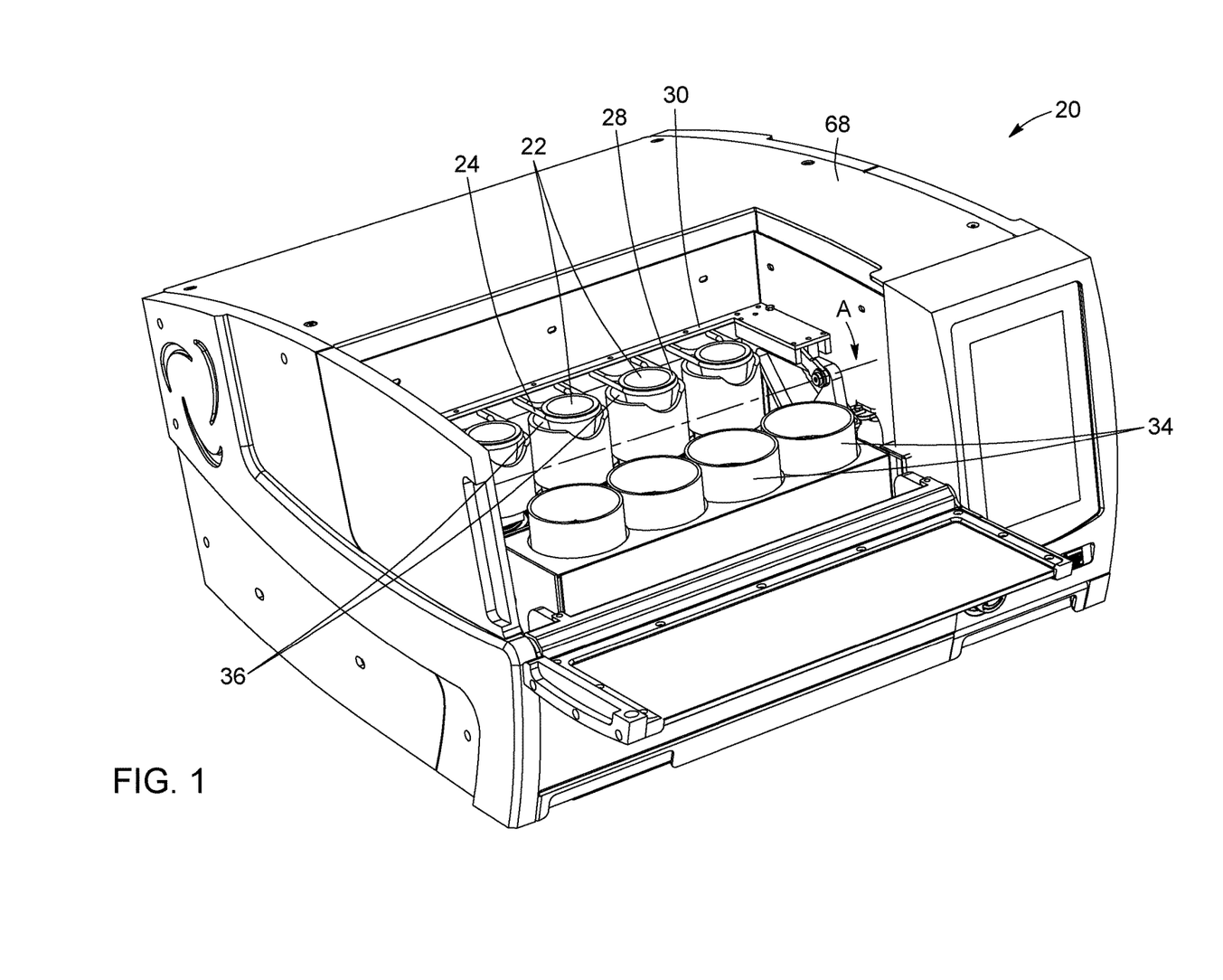
FIG. 1 is a perspective view of an embodiment of the apparatus for preparing analytical samples by fusion, according to the invention.
Figure 2:
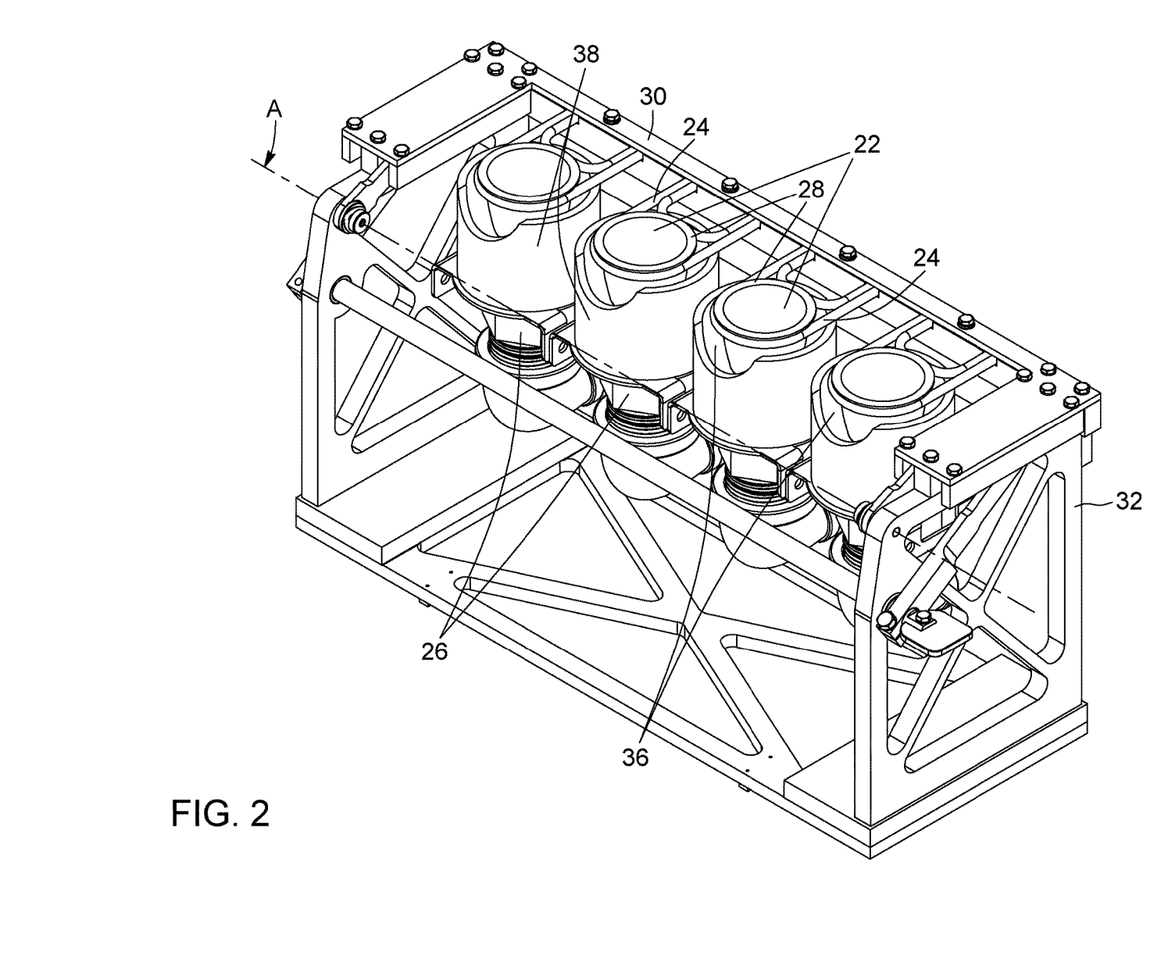
FIG. 2 is a perspective view of an embodiment of the apparatus of FIG. 1.

Referring to FIGS. 1 and 2, there is schematically illustrated a fluxer 20 which is an exemplary apparatus for preparing analytical samples by fusion. The fluxer 20 shown is a gas fluxer, wherein heating is provided by combustion of a gas such as natural gas. It is understood that the fluxer 20 can alternatively be an electrical fluxer, wherein heating is provided using an electrical resistor or a susceptor.

The fluxer 20 includes crucibles 22 for receiving a sample and a flux material. In the configuration shown, the fluxer 20 includes four crucibles 22, but it is understood that the fluxer 20 can include only one crucible 22 or a number of crucibles 22. The crucible 22 is made of components which can withstand the high temperatures required to prepare the analytical sample, without contaminating the analytical sample. In some implementations, the crucible 22 is made of a Pt—Au alloy. The crucible 22 can have a generally inversely frusto-conical shape, but can also have other shapes.

In some implementations, each crucible 22 is supported by a corresponding crucible support 24 and heated by a corresponding heating element 26. The crucible support 24 maintains the crucible 22 in a suitable position to be heated by a corresponding heating element 26 (also referred to herein as heater 26). In the exemplary embodiment shown in FIGS. 1 and 2, the crucible 22 has a flange rim 28 and the crucible support 24 is a double U-shaped crucible support that receives and holds the crucible 22 thanks to the flange rim 28. In some implementations, the crucible support 24 is attached to a pivotable holder 30, which will be discussed further below.

The heating element 26 is configured to heat the crucible and fuse the sample and flux material to obtain a fused mixture. In some implementations, the heating element 26 is a gas burner located under the crucible 22. In some implementations, the heating element 26 includes a controller to control the energy provided to the crucible. For example, the intensity of the flame from the gas burner can be controlled depending on the sample to be analyzed, the flux material and the desired heating power.

Still referring to FIGS. 1 and 2, the fluxer 20 includes a stirring unit for stirring the fused mixture in the crucible. In the embodiment shown, the pivotable holder 30 (to which are attached the crucible supports 24) is attached to a movable assembly 32 providing the stirring. For example, the movable assembly 32 can move in a plane substantially perpendicular to the flame of the gas burner 26, thereby providing the stirring by a movement of rotation or orbital motion. In such a configuration, the movement of the movable assembly 32 induces movement of the crucibles 22, which allows for the contents of the crucibles 22 to be mixed together. An advantage of this stirring unit can be that the contents of each crucible 22 are mixed in the same manner, as the movement of each crucible 22 is the same. Of course, it is understood that the stirring unit can be different than the stirring unit described above, as long as the fused mixture obtained is substantially homogeneous. For example, the stirring unit can be embodied by independent stirring elements each one being associated with a corresponding one of the crucibles 22. Hence each of the stirring elements induces a movement (e.g. rotation and/or rocking) to its corresponding crucible 22.

In some implementations, the pivotable holder 30 can be pivoted about axis A and towards containers 34 to pour the fused mixture from the crucibles 22 into the containers 34. The containers 34 can be beakers that can contain a solution in which the homogneous fused mixture is poured to prepare analytical samples suitable for analysis by AA, ICP or other wet chemistry techniques. Alternatively, a mould can be placed instead of each container 34. In such a case, the homogeneous fused mixture is poured into the mould and cooled, for example to room temperature, to obtain an analytical sample suitable for XRF analysis.

Figure 4:
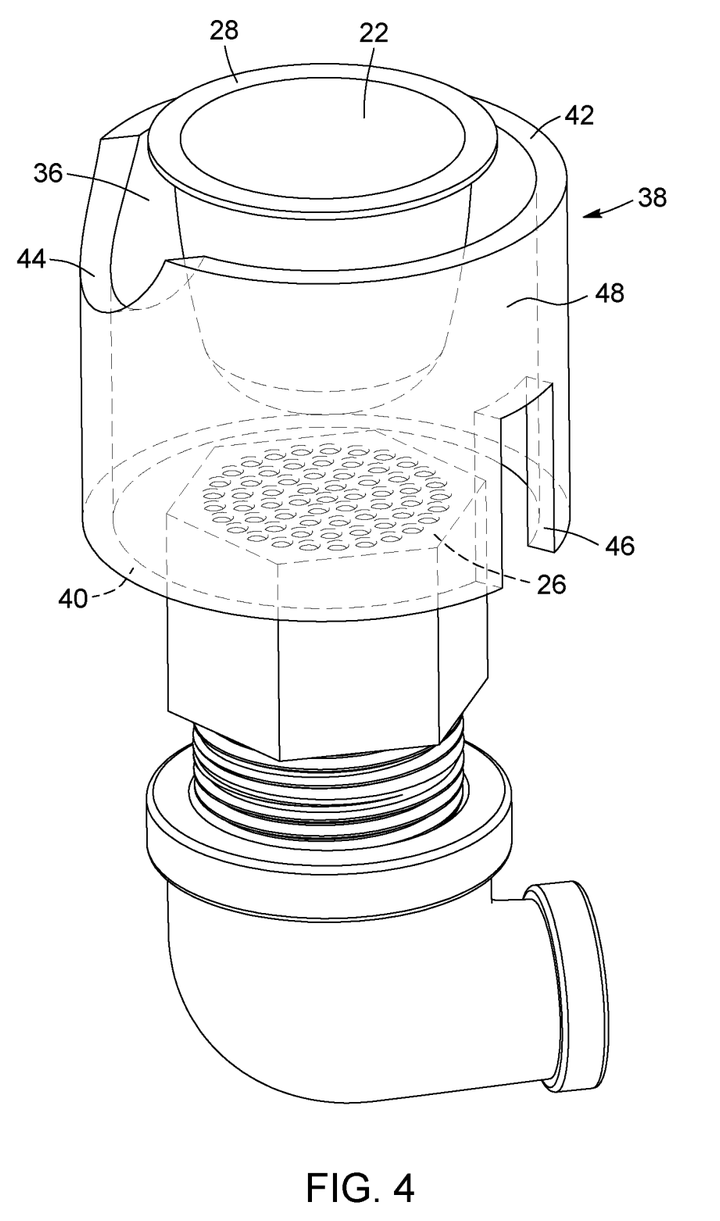
FIG. 4 is a perspective view of a hollow tube used in an embodiment of the apparatus according to the invention.

Referring to FIG. 4, the fluxer 20 includes a reflective and/or heat-conducting surface 36 (also simply referred to herein as "surface" 36) provided at a distance from each one of the crucibles 22. In some implementations, the surface 36 is also provided around of the crucible 22 (i.e., the surface 36 surrounds the crucible 22). The surface 36 can reflect a first portion of heat radiation radiating from the crucible 22 back to the crucible 22, so as to provide additional heat to fuse the mixture. The surface 36 can also absorb a second portion of the heat radiation radiating from the crucible 22.

It is understood that the term "surface", refers to a superficial layer of an object and that the surface 36 may be plane or curved, smooth or rough. The object of which the surface is a part of, can be of any shape or form which allows the crucible 22 to be heated by the heating element 26. It is understood that the expression "provided at a distance" means that the surface 36 and the crucible 22 are not in direct contact. It is also understood that the expressions "surrounding the crucible" or "being provided around of the crucible" mean that the exterior wall of the crucible 22 is at least partially enclosed into the object of which the surface is a part of.

In the exemplary embodiment shown in the Figures, the surface 36 is the interior surface of a hollow tube 38. The hollow tube 38 has an inside diameter greater than the base diameter of the crucible. For example, the hollow tube 38 has an inside diameter between 4 cm and 10 cm, and an outside diameter between 5 cm and 11 cm. The distance between the crucible and the surface 36 can vary across the length of the crucible and can for example be between 0.2 cm and 5 cm. The hollow tube 38 has a lower end 40 and an upper end 42 and is mounted around the crucible such that the lower end 40 extends substantially at the level of the heating element 26, and the upper end 42 extends below the flange rim 28 such that the crucible support 24 is not in direct contact with the upper end 42. The hollow tube 38 can for example be attached to the movable assembly 32 or to another fixed element of the fluxer 20, and the length of the hollow tube can be between 3 cm and 15 cm.

Optionally, the hollow tube 38 can be provided with trench, a recess and/or a groove (or more generally a cut in the hollow tube), such as trench 44 and groove 46 as shown in FIG. 4. For example, the groove 46, which can allow for air to circulate more easily towards the gas burner 26, is an elongated cut extending from the lower end 40 of the hollow tube 38. The trench 44 can be provided to accommodate the crucible 22 when the pivotable holder 30 is rotated to pour the homogeneous fused mixture into the container 34. For example, the trench 44 is a half-circular cut into the upper end 42 of the hollow tube 38.

In some implementations, the surface 36 (and/or the hollow tube 38) is made of a heat-resistant metal such as a heat-resistant stainless steel or a heat-resistant superalloy. For example, the heat-resistant metal can be an austenitic nickel-chromium-based stainless steel such as Inconel® or Nikrothal®, or a ferritic iron-chromium-aluminium alloy such as Kanthal® APM. Optionally, the external surface 48 of the hollow tube 38 can be coated with an insulating ceramic coating such as Cerakote® to improve heat resistance and heat insulation of the hollow tube 38.

Figure 6:
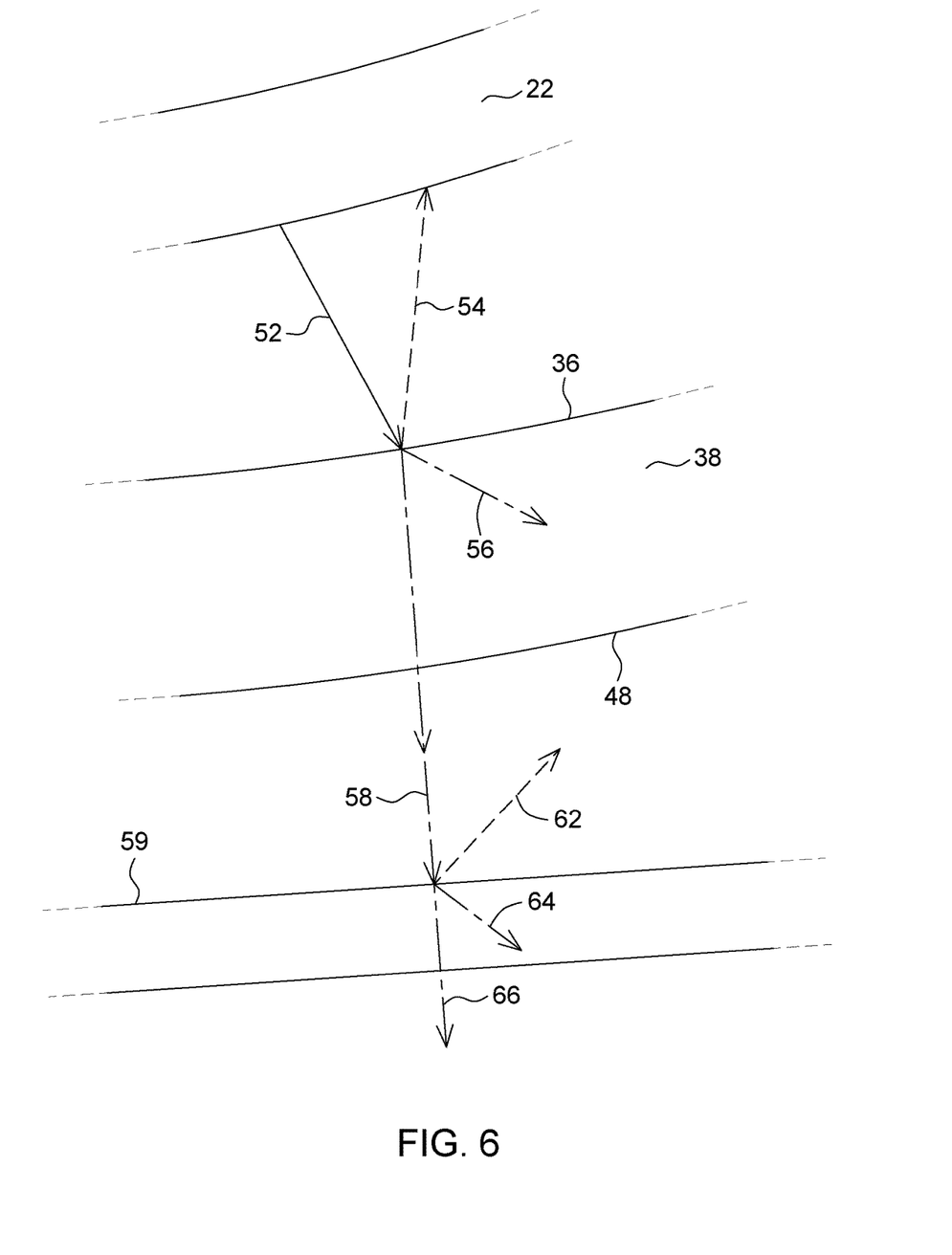
FIG. 6 is a schematic representation of the reflected, absorbed and transmitted heat according to an embodiment of the invention.

Now referring to FIG. 6, when the crucible 22 is heated to fuse the sample and the flux material therein, heat radiation 52 radiates from the crucible 22 and strikes the surface 36 of the hollow tube 38. The heat radiation 52 is then divided into (i) reflected heat radiation 54 which is reflected by the surface 36 back to the crucible 22; (ii) absorbed heat radiation 56 which is absorbed by the surface 36 and into the hollow tube 38, thereby heating the hollow tube 38; and (iii) transmitted heat radiation 58 which is transmitted by the external surface 48 of the hollow tube 38. The reflected heat radiation 54 provides additional heat to the crucible 22 to fuse the mixture in the crucible 22. Such a configuration can reduce the energy requirements to fuse the mixture.

In known systems including a plurality of adjacent crucibles, but not having the reflective and/or absorptive surface 36 surrounding the crucibles, heat radiation radiating from each crucible can be absorbed into adjacent crucibles. As such, when the same amount of energy is provided to each crucible, a heated crucible which has two neighboring crucibles is typically at a higher temperature than a crucible which only has one neighboring crucible. While providing the surface 36 around each crucible partly solves this issue, in some scenarios, enough transmitted heat 58 can be transmitted past the hollow tube 38 to heat an adjacent crucible, thereby affecting the temperature of the adjacent crucible during preparation of the analytical sample.

Figure 3:
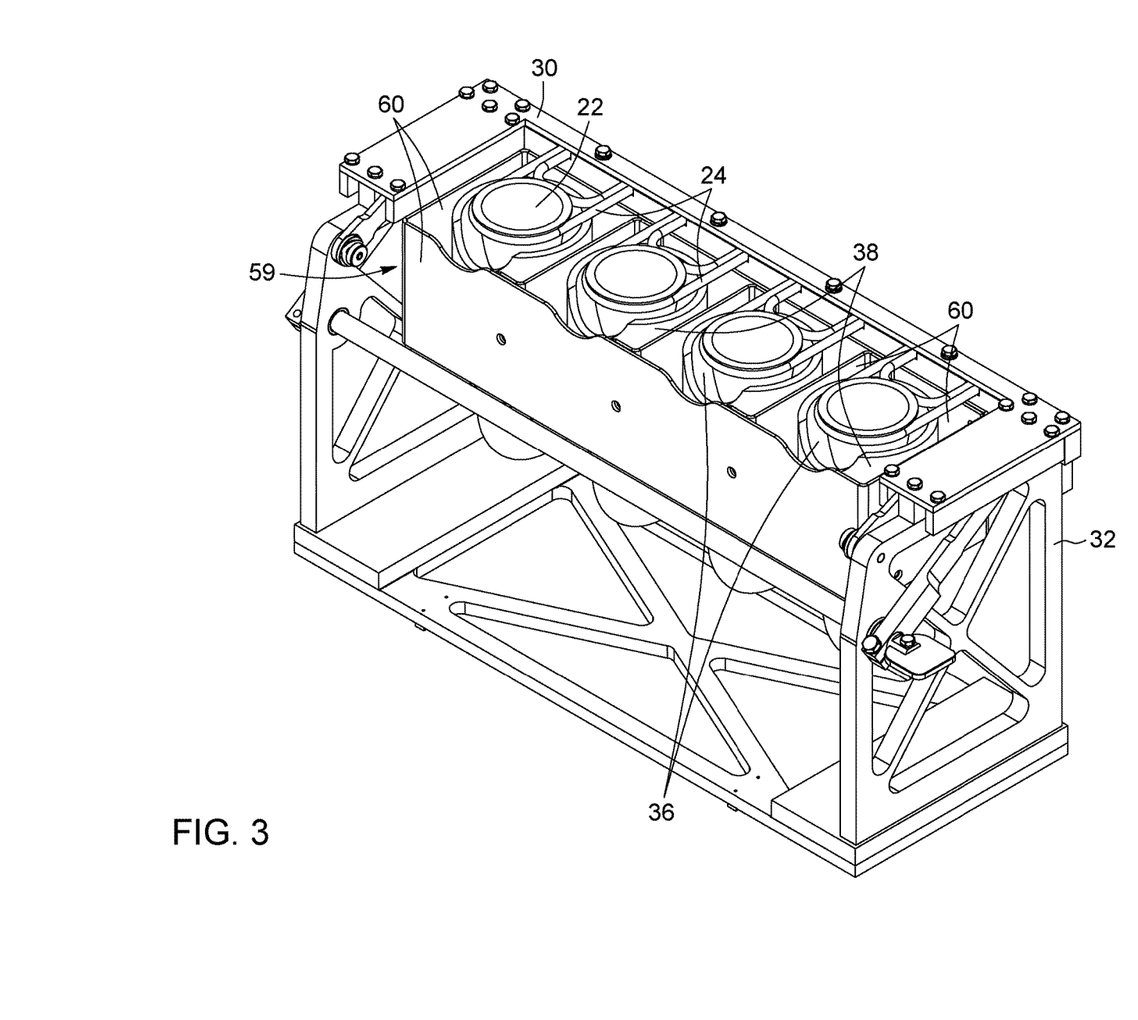
FIG. 3 is a perspective view of the interior portion of the apparatus according to another embodiment of the invention.
Figure 5:
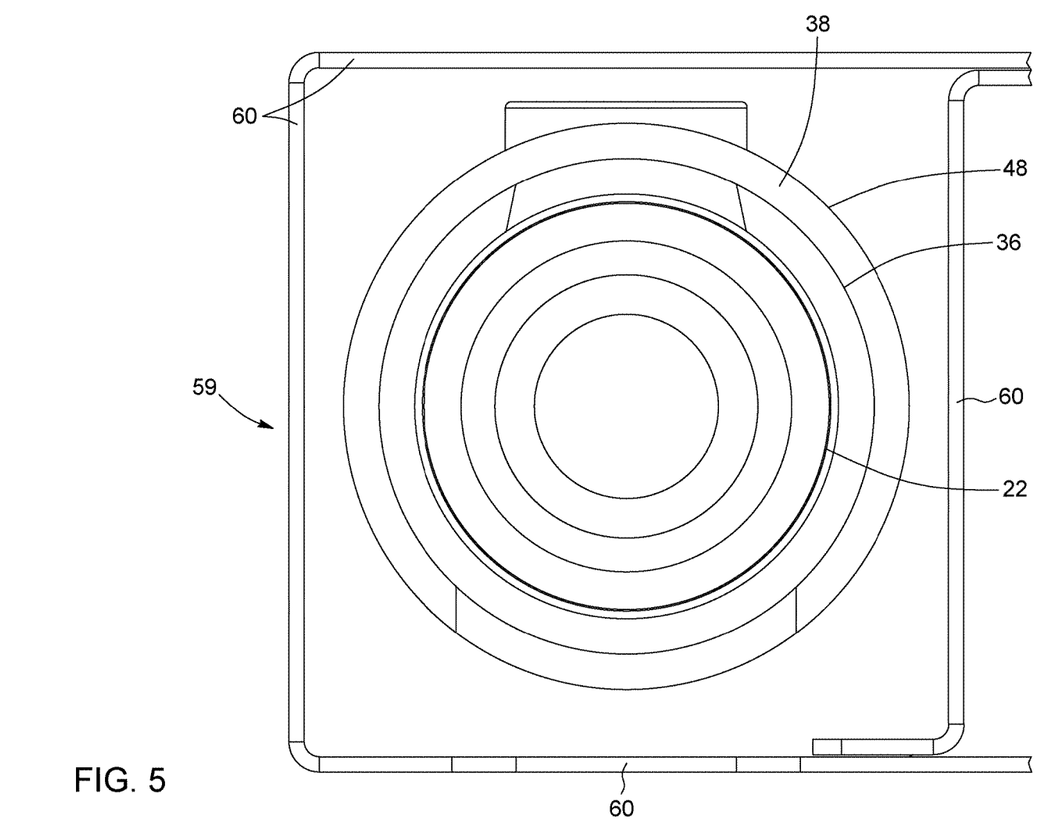
FIG. 5 is a top partial view of the apparatus of FIG. 3.

Now referring to FIGS. 3 and 5, when the fluxer 20 includes a plurality of crucibles 22 with corresponding heating elements 26 and hollow tubes 38, the fluxer 20 can further include an insulating surface 59 surrounding each one of the hollow tubes 38 to thermally insulate the crucibles 22 and the hollow tubes 38 from one another. For example, the insulating surface 59 can be embodied by a plurality of insulating plates 60, which can be made of a highly heat-reflective material such as aluminum.

Referring back to FIG. 6, the transmitted heat radiation 58 is absorbed into the insulating surface 59 and is then divided into (i) secondary reflected heat radiation 62 which is reflected towards the hollow tube 38; (ii) secondary absorbed heat radiation 64; and (iii) secondary transmitted heat radiation 66. When the insulating surface 59 is made of a highly reflective material such as aluminum, the secondary reflected heat radiation 62 can include most of the energy of the transmitted heat radiation 58. In such a case, the secondary absorbed heat radiation 64 and secondary transmitted heat radiation 66 are negligible.

In some implementations, the fluxer 20 further includes a temperature sensor for measuring the temperature of the hollow tube 38 (or more generally, the temperature of the object including the surface 36). For example, the temperature can be measured on the external surface 48 of the hollow tube 38 and/or on the internal surface 36 of the hollow tube 38. The temperature sensor can be a thermocouple, for example suitable for measuring temperatures of up to 750° C.

Optionally the fluxer 20 can further include a processor for calculating the temperature of the crucible 22 from the temperature of the hollow tube 38 (or more generally, from the temperature of the object including the surface 36) in accordance with a predetermined correlation between the temperature of the crucible 22 and the temperature of the surface 36, 38. Optionally, the fluxer 20 can further include a temperature controller for adjusting the temperature of the crucible to a target temperature. It is understood that the expression "temperature of the crucible" can refer to the temperature of the outer wall of the crucible, the temperature of the inner wall of the crucible, or the temperature of the melted mixture (also referred to herein as the "melt") within the crucible.

In the embodiments illustrated, the fluxer (20) comprises a casing 68 in which the crucible support 24, the holder 30 and the crucibles 22 are mounted. It is understood that the processor can be contained within the casing 68 or be provided in a separate processing unit operatively connected to the temperature sensor of fluxer 20, such as a computer.

In another general aspect, there is provided a method for preparing an analytical sample by fusion.

The method includes heating and stirring, in a crucible, a mixture of a sample and a flux material at a temperature sufficient to fuse the mixture and obtain a substantially homogeneous mixture. In some implementations the heating and stirring of the mixture can be performed by directly heating and stirring the crucible. As explained above, the heating of the mixture can for example be performed by directly heating the crucible with a flame of a gas burner, and the stirring of the mixture can for example be performed by stirring the crucible (i.e., rotating or rocking the crucible). Alternatively, in some implementations, the heating of the mixture can be performed by indirect heating of the crucible, for example by conduction or heat radiation, using a resistor or a susceptor.

In some implementations, while heating and stirring the mixture, the method includes reflecting a first portion of heat radiation radiating from the crucible back to the crucible so as to provide additional heat to fuse the mixture. Reflecting the first portion of the heat radiation can be performed by providing a reflective surface around of and at a distance from the crucible, as explained above.

In some implementations, the method includes indirectly measuring the temperature of the crucible. The indirect measurement of the temperature of the crucible includes absorbing at least a portion of heat radiation radiating from the crucible into a heat-conducting surface provided at a distance from the crucible. It is understood that the "heat-conducting surface" can be the same as or be different than the reflective surface referred to above.

The indirect measurement of the temperature of the crucible also includes measuring the temperature of the surface. In some implementations, the temperature of the heat-conducting surface is measured using a thermocouple, but the temperature of the surface can also be measured using any suitable temperature measurement means, such as a pyrometer or an infrared thermometer.

The indirect measurement of the temperature of the crucible also includes calculating the temperature of the crucible from the temperature of the heat-conducting surface in accordance with a predetermined correlation between the temperature of the crucible and the temperature of the heat-conducting surface. By "predetermined correlation", it is meant that the correspondence between the temperature of the crucible and the temperature of the heat-conducting surface is measured prior to performing the method. In other words, prior to proceeding with the method, the apparatus has to be calibrated. Indeed the predetermined correlation can be obtained for a given set of parameters, and the correspondence between the temperature of the heat-conducting surface and the temperature of the crucible can be calculated therefrom, provided that the set of parameters during the measurement of the temperature of the heat-conducting surface is the same as the set of parameters used during the initial correlation. For example, the set of parameters can include the material forming the crucible, the material forming the heat-conducting surface, the shape of the heat-conducting surface, the distance between the heat-conducting surface and the crucible, the location of the temperature sensor on the heat-conducting surface, the type of temperature sensor and so on. In some implementations, the predetermined correlation is stored in a computer readable storage medium.

In some implementations, the method includes an adjustment of the temperature of the crucible to a target temperature. As explained above, it can be desirable to control the temperature of the fused mixture so as to not heat the fused mixture substantially above 1100° C. Furthermore, when multiple analytical samples of the same material are to be analyzed, heating the mixture to the same temperature and for the same amount of time typically leads to more reliable and reproducible analyses. In some implementations, the adjustment of the temperature of the crucible can include comparing the indirect temperature measurement to the target temperature, and consequently adjusting the heating to either lower or increase the temperature of the crucible. A feedback loop can optionally be implemented to automatically regulate the temperature of the crucible depending on the indirect temperature measurement.

The method also includes cooling the substantially homogeneous fused mixture, thereby forming the analytical sample. The cooling of the substantially homogeneous fused mixture can for example include letting the substantially homogeneous fused mixture cool to ambient temperature. Alternatively, the substantially homogeneous fused mixture can be cooled by pouring the substantially homogeneous fused mixture into a solution. In some implementations, the substantially homogeneous mixture is poured into a mould and cooled by air blowing. For example, a ventilation system can blow air on the poured homogeneous mixture to speed up the cooling. The air can be pressurized air.

It is appreciated that features of the implementations described herein can be combined with other implementations or alternatives thereof.

Moreover, although the implementations of the apparatus described herein can consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, may be used for the apparatus, as it will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

EXAMPLE

Experiments were performed to correlate the temperature of a heat-conducting surface of a hollow tube located around a crucible of a gas fluxer, with the temperature of a melt within the crucible. A first type R thermocouple was placed in the melt and a second type R thermocouple was placed on the inner wall of the hollow tube surrounding the crucible.

The crucible was heated for 10 minutes (600 seconds) and the melt was agitated at 160 rpm. The gas fluxer was set to heat at 50% of the maximum heating power. The initial temperature of the hollow tube was set at ambient temperature.

Figure 7:
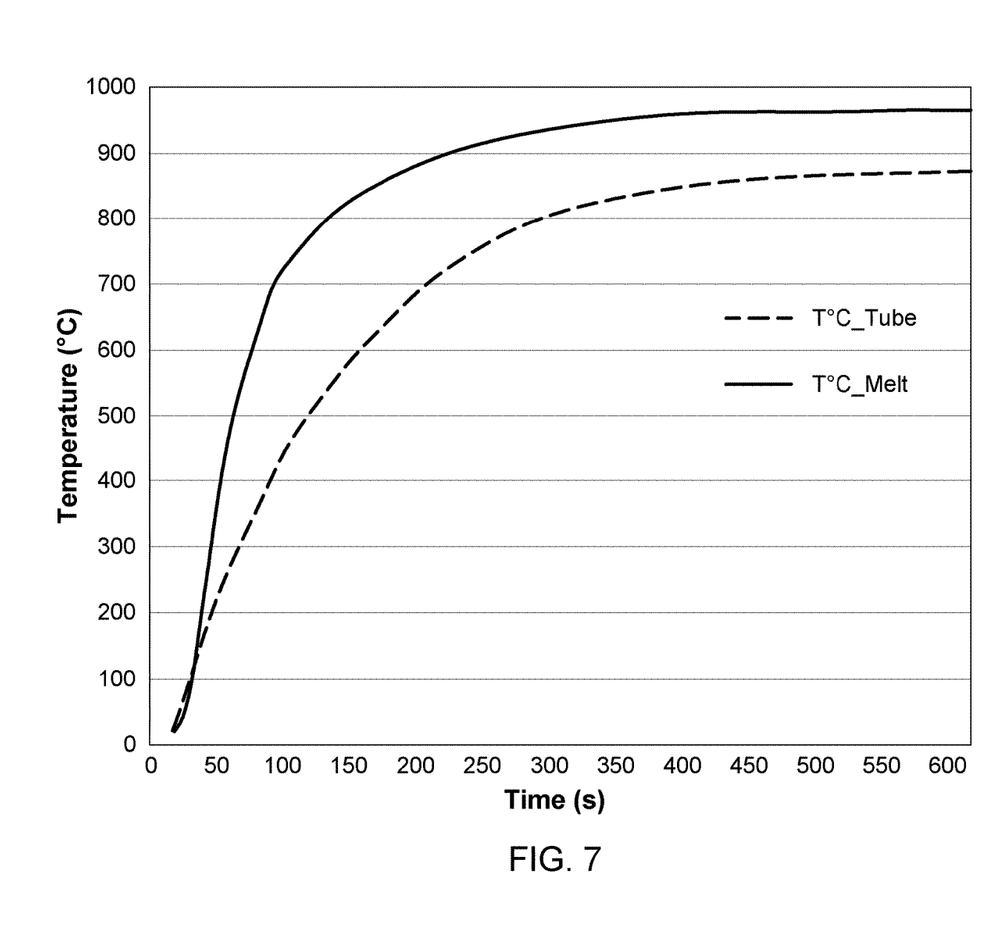
FIG. 7 is a plot showing a correlation between the temperature of a melt within a crucible and the temperature of a hollow tube surrounding the crucible.

A correlation is shown on FIG. 7. The plots showing the temperature of the hollow tube were obtained by directly measuring the temperature of the hollow tube. The plots showing the temperature of the melt were obtained by directly measuring the temperature of the melt and smoothing the curve obtained.

It is understood that the correlation shown is for illustration purposes only, and that other correlations can be performed in a similar manner, by modifying certain parameters. For example, by modifying the positioning/type of the temperature sensors, the alloy used for the crucible and/or the shape of the crucible, the composition and/or the shape of the hollow tube, the heating power of the fluxer and/or the positioning of the hollow tube with respect to the crucible, the correlation plots can vary. Using correlation curves, a user can determine the temperature of the melt by measuring the temperature of the hollow tube.

The invention claimed is:

1. A method for preparing an analytical sample by fusion for X-ray fluorescence (XRF), atomic absorption (AA) or inductively induced plasma (ICP) analysis, the method, comprising:

heating and stirring, in a crucible, a mixture of a sample and a flux material at a temperature sufficient to fuse the mixture and obtain a substantially homogeneous fused mixture, wherein the flux material is a salt having a melting temperature lower than the melting temperature of the sample;

while heating and stirring the mixture, reflecting a first portion of heat radiation radiating from the crucible back to the crucible using a heat-conducting and reflective surface provided around of and at a distance from the crucible, so as to provide additional heat to fuse the mixture;

indirectly measuring the temperature of the crucible, comprising:

absorbing a second portion of the heat radiation radiating from the crucible into a heat-conducting and reflective surface;

measuring the temperature of the heat-conducting and reflective surface;

calculating the temperature of the crucible from the temperature of the heat-conducting and reflective surface in accordance with a predetermined correlation between the temperature of the crucible and the temperature of the heat-conducting and reflective surface; and cooling the substantially homogeneous fused mixture, thereby forming the analytical sample.

2. The method of claim 1, wherein the distance is between 0.2 cm and 5 cm.

3. The method of claim 1, wherein the heat-conducting and reflective surface is an inner surface of a hollow tube.

4. The method of claim 1, wherein the measuring of the temperature of the heat-conducting and reflective surface is performed using a temperature sensor provided on the heat-conducting and reflective surface.

5. The method of claim 1, wherein the flux material is lithium tetraborate, lithium metaborate or a mixture thereof.

6. The method of claim 1, wherein the heating is provided by combustion of a gas.

7. The method of claim 1, wherein the heating is provided by an electrical resistor or susceptor.

8. An apparatus for preparing an analytical sample by fusion for X-ray fluorescence (XRF), atomic absorption (AA) or inductively induced plasma (ICP) analysis, the apparatus, comprising:
   a crucible for receiving a mixture of a sample and a flux material, wherein the flux material is a salt having a melting temperature lower than the melting temperature of the sample;
   a crucible support for supporting the crucible;
   a heater configured to heat the crucible and fuse the mixture to obtain a fused mixture;
   a stirring unit for stirring the fused mixture in the crucible;
   a heat-conducting and reflective surface provided around of and at a distance from the crucible, to reflect a first portion of heat radiation radiating from the crucible back to the crucible and absorb a second portion of the heat radiation radiating from the crucible; and
   a temperature sensor for measuring the temperature of the heat-conducting and reflective surface.

9. The apparatus of claim 8, wherein the distance is between 0.2 cm and 5 cm.

10. The apparatus of claim 8, wherein the heat-conducting and reflective surface is an inner surface of a hollow tube surrounding the crucible.

11. The apparatus of claim 10, further comprising an insulating surface surrounding the hollow tube to insulate the hollow tube.

12. The apparatus of claim 11, wherein the insulating surface is made of aluminium.

13. The apparatus of claim 10, wherein the hollow tube has an outer insulating surface made of an insulating material to insulate the hollow tube.

14. The apparatus of claim 13, wherein the outer insulating surface is made of an insulating ceramic material.

15. The apparatus of claim 8, wherein the temperature sensor comprises a thermocouple attached to the heat-conducting and reflective surface.

16. The apparatus of claim 8, further comprising a processor for calculating the temperature of the crucible from the temperature of the heat-conducting and reflective surface in accordance with a predetermined correlation between the temperature of the crucible and the temperature of the heat-conducting surface.

17. The apparatus of claim 8, wherein the flux material is lithium tetraborate, lithium metaborate or a mixture thereof.

18. The apparatus of claim 8, wherein the heater operates by combustion of a gas.

19. The apparatus of claim 8, wherein the heater is an electrical resistor or a susceptor.

20. An apparatus for preparing an analytical sample by fusion for X-ray fluorescence (XRF), atomic absorption (AA) or inductively induced plasma (ICP) analysis, the apparatus, comprising crucibles for receiving a mixture of a sample and a flux material, wherein the flux material is a salt having a melting temperature lower than the melting temperature of the sample, wherein the apparatus further comprises, for each one of the crucibles:
   a crucible support for supporting a corresponding crucible;
   a heater configured to heat the corresponding crucible and fuse the mixture to obtain a fused mixture;
   a stirring unit for stirring the fused mixture in the corresponding crucible;
   a heat-conducting and reflective surface provided around of and at a distance from the corresponding crucible, the heat-conducting and reflective surface reflecting a first portion of heat radiation radiating from the corresponding crucible back to the corresponding crucible and absorbing a second portion of the heat radiation radiating from the corresponding crucible; and
   a temperature sensor for measuring the temperature of the heat-conducting and reflective surface.

21. The apparatus of claim 20, wherein the heat-conducting and reflective surface is an inner surface of a hollow tube surrounding the corresponding crucible.

22. The apparatus of claim 20, further comprising an insulating surface surrounding the hollow tube to insulate the hollow tube.

23. The apparatus of claim 20, wherein the temperature sensor comprises a thermocouple attached to the heat-conducting and reflective surface.

* * * * *